(12) United States Patent
Porcher

(10) Patent No.: US 10,434,257 B2
(45) Date of Patent: Oct. 8, 2019

(54) POWERED INJECTION DEVICE FOR DELIVERING MULTIPLE LIQUID FORMULATIONS, INCLUDING VACCINES

(71) Applicant: BOEHRINGER INGELHEIM ANIMAL HEALTH USA INC., Duluth, GA (US)

(72) Inventor: Ludovic Porcher, Quilly (FR)

(73) Assignee: BOEHRINGER INGELHMEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/487,308

(22) Filed: Apr. 13, 2017

(65) Prior Publication Data

US 2017/0296749 A1   Oct. 19, 2017

Related U.S. Application Data

(60) Provisional application No. 62/322,072, filed on Apr. 13, 2016.

(51) Int. Cl.
| | |
|---|---|
| *A61M 5/20* | (2006.01) |
| *A61M 5/19* | (2006.01) |
| *A61M 5/315* | (2006.01) |
| *A61M 5/145* | (2006.01) |
| *A61D 1/02* | (2006.01) |
| *A61M 5/32* | (2006.01) |

(52) U.S. Cl.
CPC ........... *A61M 5/2066* (2013.01); *A61D 1/025* (2013.01); *A61M 5/14526* (2013.01); *A61M 5/19* (2013.01); *A61M 5/2053* (2013.01); *A61M 5/31501* (2013.01); *A61M 5/31513* (2013.01); *A61M 5/31578* (2013.01); *A61M 5/3298* (2013.01); *A61M 2250/00* (2013.01)

(58) Field of Classification Search
CPC .. A61M 5/2066; A61M 5/14526; A61M 5/19; A61M 5/2053
USPC .......................................................... 604/24
See application file for complete search history.

(56) References Cited

U.S. PATENT DOCUMENTS

| | | | |
|---|---|---|---|
| 4,057,334 A | 11/1977 | Ishikawa et al. | |
| 4,863,443 A * | 9/1989 | Hornung | A61D 1/025 128/200.14 |
| 4,940,460 A * | 7/1990 | Casey, I. | A61M 5/30 604/131 |
| 5,015,233 A * | 5/1991 | McGough | A61M 5/00 222/389 |
| 5,311,841 A * | 5/1994 | Thaxton | A61D 1/025 119/174 |
| 5,807,340 A | 9/1998 | Pokras | |
| 2005/0263079 A1 * | 12/2005 | Karaca | A01K 45/007 119/6.8 |

(Continued)

FOREIGN PATENT DOCUMENTS

FR    2930425 A1 * 10/2009 ............. A61D 1/025

*Primary Examiner* — Edelmira Bosques
(74) *Attorney, Agent, or Firm* — Judy Jarecki-Black; Patrick Lowder

(57) ABSTRACT

The invention relates to hand-held, powered injection devices, for administering fluids, including vaccines, to animals. The invention further relates to methods of use of the powered injection device for vaccinating avian animals. Powered injection devices according to the instant disclosure are ergonomically friendly, and offer rapid and consistent dosing, particularly for avian animals.

16 Claims, 18 Drawing Sheets

(56) References Cited

U.S. PATENT DOCUMENTS

| | | | |
|---|---|---|---|
| 2007/0197963 A1* | 8/2007 | Griffiths | A61M 5/007 604/97.01 |
| 2008/0177223 A1* | 7/2008 | Johnston | A61D 1/025 604/68 |
| 2010/0143864 A1 | 6/2010 | An | |

* cited by examiner

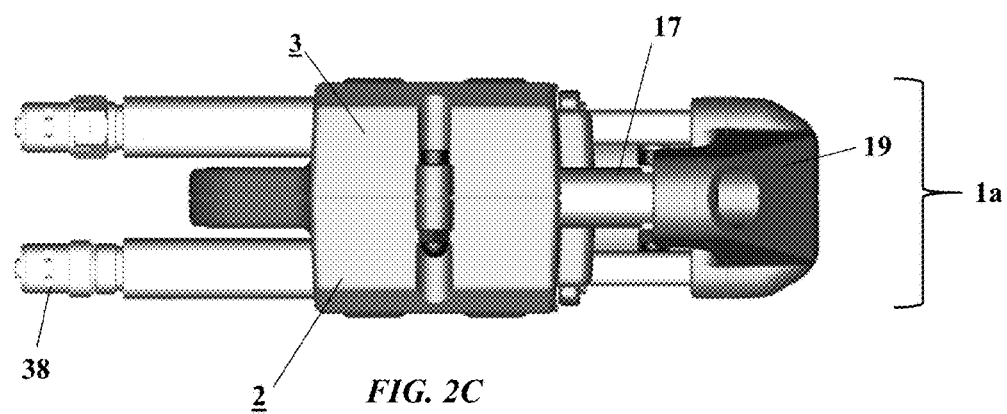
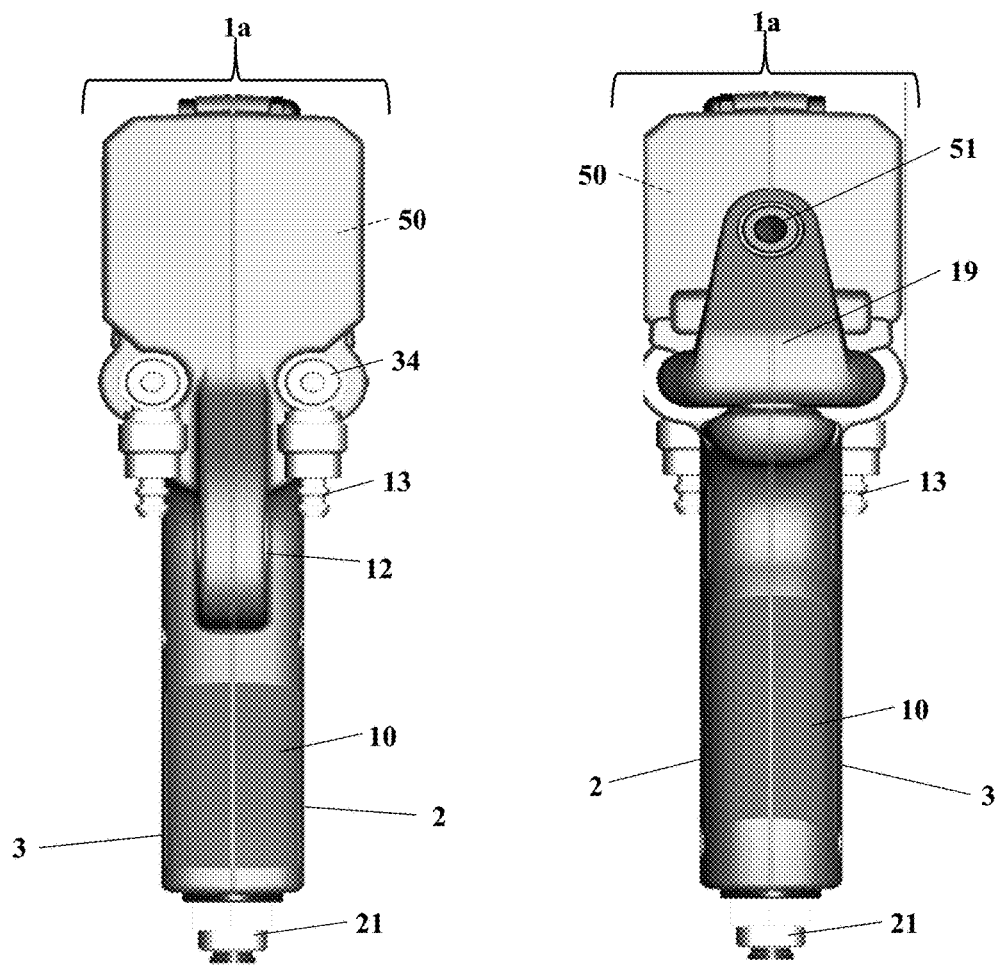
FIG. 2C
FIG. 2D
FIG. 2E

POWERED INJECTION DEVICE FOR DELIVERING MULTIPLE LIQUID FORMULATIONS, INCLUDING VACCINES

CROSS-REFERENCE TO RELATED APPLICATIONS

This application claims priority to U.S. provisional application No. 62/322,072, filed 13 Apr. 2016, which is incorporated herein by reference in its entirety.

INCORPORATION BY REFERENCE

All references cited below are herein incorporated by reference in their entirety.

FIELD OF THE INVENTION

The invention relates to a pneumatic injection device and methods of use for delivering liquid formulations, including vaccines, to animals.

BACKGROUND OF THE INVENTION

Syringes allow for vaccination of avian animals, for example, one day old chicks or older birds. Existing systems are largely manually actuated, and non-ergonomically friendly, resulting in cumbersome, slow and inefficient vaccination. There are some pneumatic syringes, but these are rarely used. They are heavy, not ergonomic and too large because the pneumatic cylinders are placed at the rear of the syringe pistons. Existing devices quickly lead to user fatigue, which can decrease the quality of the injections, leaving the animals more vulnerable to pathogens.

Applicants thus sought to develop an improved, ergonomic, powered injection device, which can deliver multiple liquid formulations simultaneously.

SUMMARY OF THE INVENTION

The instant invention is based upon the successful engineering of a powered injection device, which delivers liquid formulations, including vaccine formulations, to animals, including avian animals. In an aspect, the instant disclosure provides an improved apparatus for the rapid subcutaneous and intramuscular injection of animals, including avian animals, and, including day old chicks. The power source may be, for example, pneumatic, electric or hydraulic.

It is thus one object of the invention to provide a pneumatic injection device useful for administering fluids, including vaccine compositions to animals, including birds, by injection. The present powered injection device was designed by Applicants to facilitate injections and improve the user's experience by reducing fatigue and the incidence of "over-use" type injuries.

In an embodiment, the powered injection device comprises two injectors, allowing for the injection of two different vaccines. Importantly, multiple different pistons are provided, wherein when different sized pistons are connected to injection device, different dosage volumes are injected. As such, the user may select the same or different dosage volumes for each liquid formulation. To change the volume, the user simply selects the appropriate piston, which is engraved (or otherwise marked) to indicate what volume will be delivered when it is affixed to the injection device.

The injection device may be equipped with one or two needles to inject the vaccines. Where the formulations are compatible, a single needle for injection may be desirable. Likewise, when the vaccine formulations are less compatible, the use of two needles may be more desirable. The user may easily remove or add back the provided adaptor that allows the contents of the separate cylinders to ultimately combine into a single deliverable dose. In general, the pneumatic injection device requires a minimum air pressure of 4 bars to function properly.

In an embodiment, the apparatus comprises a powered injection device, which resembles a gun (FIG. 1). In one embodiment, the powered injection device (1) may be substantially as depicted in FIG. 1, comprising a handle (10), assembly/disassembly screws (11), a trigger (12), one or more vaccine line connectors (21), one or more injectors (30), one or more needle connecting means (38), removably connectable to one or more injector cylinder (31), an air cylinder (50) an air cylinder rod (17), one or more injection device piston sleeves (41), which circumscribe the pistons (40), a piston pusher (19), a locking means (20), and an air supply connecting means (21). Luer-lock style hypodermic needles (22), for example, may be affixed to the needle connecting means (38).

The injection device piston pusher (19) is operably connected to the air/pneumatic cylinder rod (17), which is operably connected to the air/pneumatic cylinder (50). During an injection cycle, air flows into the injection device (1) through orifice (8) of connecting means (21). The air continues through conduit (9), which is shown in FIG. 2A, and which is in fluid connection with the air/pneumatic cylinder (50). The pneumatic cylinder (50) may be any known to those of skill in the art, for example, "CCI" (Compact Cylinder ISO), which is an ISO 21287 cylinder from AVENTICS, Pneumatics. Applicants envision any suitable pneumatic cylinder may be used in the practice of the disclosed invention. Moreover, the injection device may be alternatively powered by electricity (e.g. electric motors or magnetism) or by hydraulic power systems, both of which the skilled person may routinely substitute for the currently embodied pneumatic power system.

When the trigger (12) is pulled, the air cylinder (50) pulls the piston pusher (19) toward the air cylinder (50), which, owing to its operable connectivity, moves and the piston(s) (40) to move laterally in the direction of the needles (22). The piston(s) (40) push the fluid through the injector(s) (30) and out the through the orifices in the needle connecting means (38), and finally through the needle(s) (22).

As shown in FIGS. 3A & 3B, in one embodiment, the powered injection device may comprise a body (1a) e.g. an assembly of a left housing half (2) and a right housing half (3). Other configurations are envisioned, though two housing halves are quite convenient, both for manufacturing and for end-use routine maintenance and cleaning. As indicated, the left (2) and right (3) halves are configured to fit together to form the body (1a), e.g., a complete housing for the powered injection device (1). Any suitable sealing means, including gaskets, may be added to facilitate the separation and reunification of the two housing halves.

As shown in FIG. 4A, the injector (30) may comprise a needle connecting means (38), which is operably connected to an injector cylinder (31), which is in fluid communication with the vaccine line connectors (21) and the piston (40). The piston (40) is connected to a piston securing cylinder (32), which may comprise a gripping means (33). Piston (40) is equipped with gasket (41), which sealably engages with injector cylinder (31) to maintain a seal therebetween.

The piston (40) is operably inserted into a spring (45) (see FIG. 8B), and circumscribed by a piston sleeve (41). The piston (40) and the sleeve (41) are secured to the piston securing means (32) via fastening of the piston nut (44). As shown, the rear portion of the injector (30), which is essentially the piston sleeve (43) and piston nut (44) is insertably connected to the piston pusher (19), which is connected to the air cylinder rod (17), which is connected to the air cylinder (50). In this way, the injector (30) is operably connected to the air/pneumatic cylinder (50).

Accordingly, when the piston (40) moves from a starting position to an ending position, vaccine or other fluid moves from the injector cylinder (31) out through the needle connecting means (38). Conversely, when the piston (40) moves from an ending position to a starting position, vaccine or other fluid moves from the vaccine line connector into the injector cylinder. In each case, the system of springs (35 & 25) and ball bearings (36 & 24) serves as one-way valves, preventing fluid from escaping via the fluid line (21) during injection, and, allowing fluid to be drawn in from the fluid line (21) when the piston is moving from its ending (injection) position to its starting (resting) position. The volume delivered is dependent upon which type of piston (40) is selected, so the user must be able to easily change from one type of piston (40) to another.

Accordingly, it is an object of the invention to not encompass within the invention any previously known product, process of making the product, or method of using the product such that Applicant reserves the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (51 U.S.C. § 112, first paragraph) or the EPO (Article 83 of the EPC), such that Applicant reserves the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may be best understood in conjunction with the accompanying drawings, in which:

FIG. 2C shows a top view of the device (1);

FIG. 2D shows a front view of the device (1);

FIG. 2E shows a rear view of the device (1);

DETAILED DESCRIPTION

Figure 1:
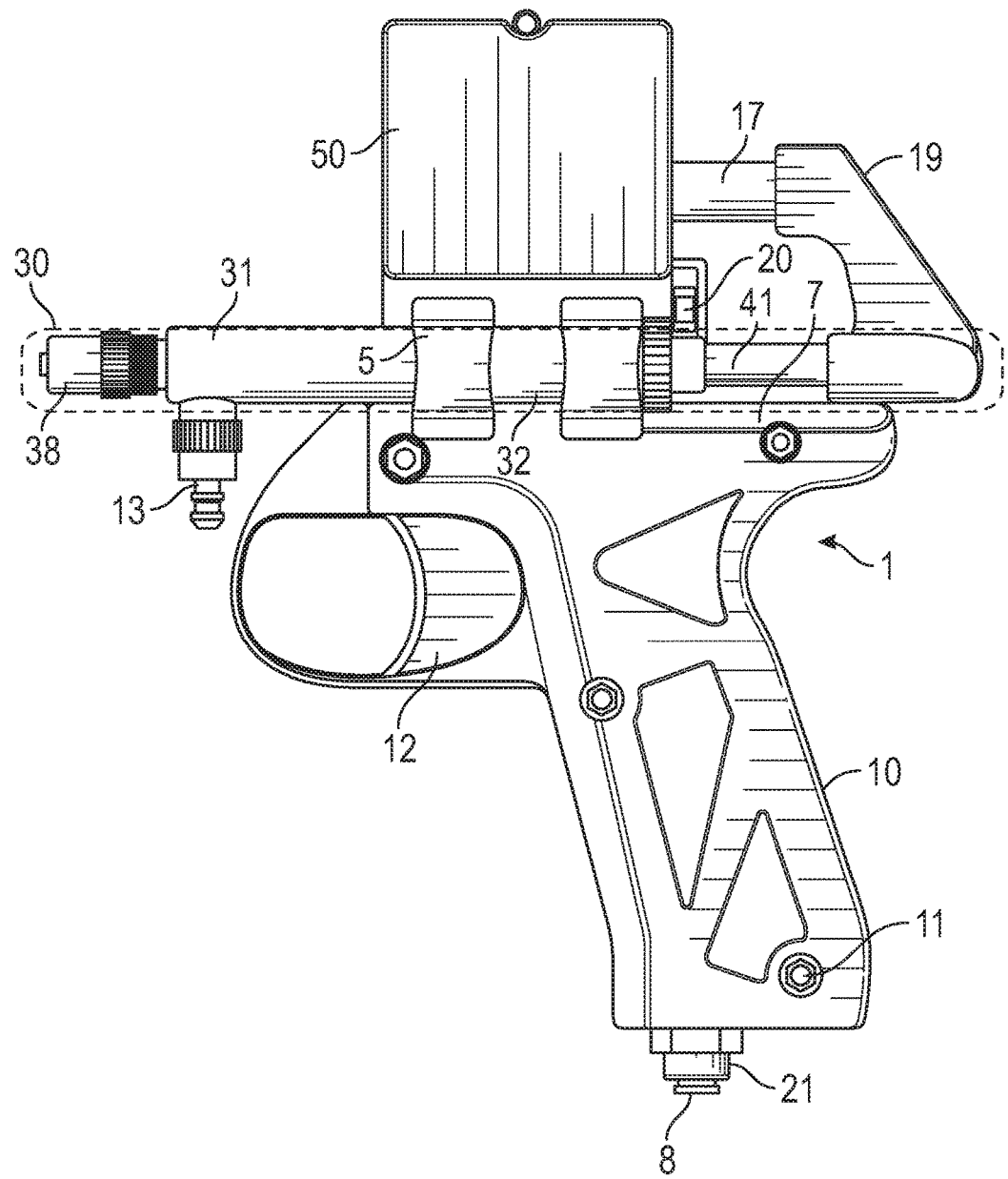
FIG. 1 shows a powered injection device (1) according to the present disclosure.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise. Finally, "about" has the ordinary meaning of "plus or minus 10%."

In one aspect, the present invention provides a powered injection device, with improve ergonomic function as compared to existing devices. In some embodiments, the power is in the form of pressurized air (i.e. a pneumatically powered device). In other embodiments, the power may be electric or hydraulic. In one particular embodiment, the device is powered by pneumatic energy, which drives a pneumatic actuator to evenly and effectively move pistons, which deliver liquid formulations, including vaccine formulations, to the device's needles, thereby injecting the formulations.

In one embodiment, the injection device has two injectors and can perform two injections at the same time. Each injector is independent and can inject equal or different volumes, depending upon which piston is selected by the device's user. At the "exit" end of the injectors, an adaptor/connector may be added to combine the fluid from both individual injectors, allowing for only a single terminal needle for injecting into the animals. This adaptor/connector may be used when the separate fluids are compatible. When the fluids are incompatible, the use of two needles, one at the exit end of each injector, is more advantageous.

As such, the disclosed powered injection device has distinct functional advantages over existing devices. The device is compact, ergonomic and provides for exceedingly precise and consistent dosing/injection. Importantly, it comprises an "intermediate push component," or "piston pusher" (19), which operably links the pneumatic/air cylinder (50) and the injector pistons (40). Moreover, the guiding means (7) restricts unwanted motion (i.e. that resulting from the indirect application of force from the pneumatic cylinder to the injector pistons), thereby providing for a controlled, linear motion during the injection cycle. As an added benefit, the combination of the guidance, intermediate push, and overall compensation system components, reduces friction, which increases the useful lifespan of the wear parts.

The advanced design of the device has allowed it to be compact, handy and lightweight. As a result of novel and inventive engineering choices, the disclosed injection device uses a single pneumatic cylinder to manage two injectors, each of which may be equipped with multiple sized pistons, depending upon the desired injection volume. Further, positioning the pneumatic cylinder above the injectors, as opposed to behind them, reduces the length of the device, and contributes to its overall compactness, making the device well-balanced, and easily manageable. One of the key distinguishing features of the disclosed device is the "top" positioning of the pneumatic air cylinder (50).

Figure 2A:
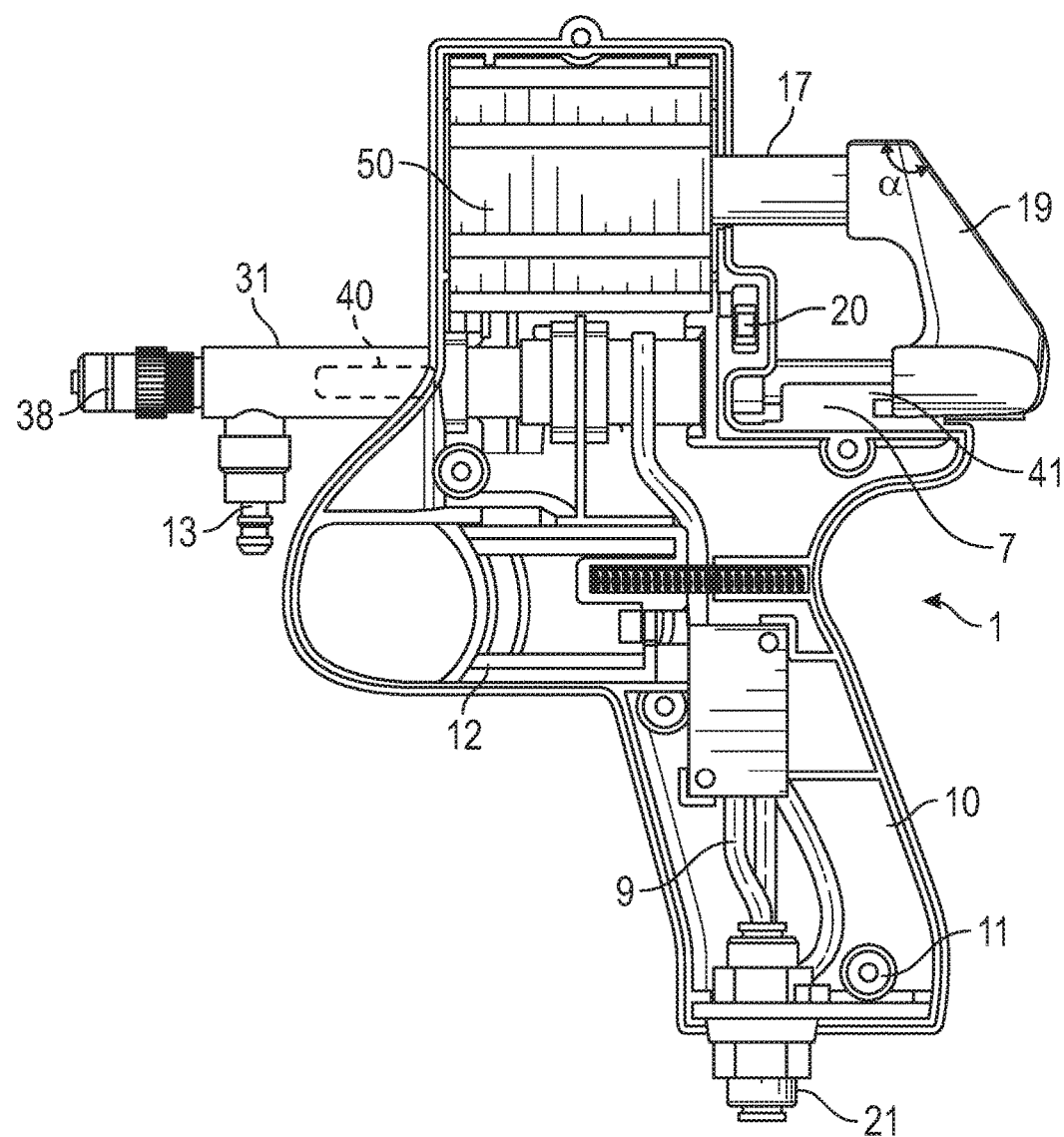
FIG. 2A shows an internal view of the injection device (1)
Figure 2B:
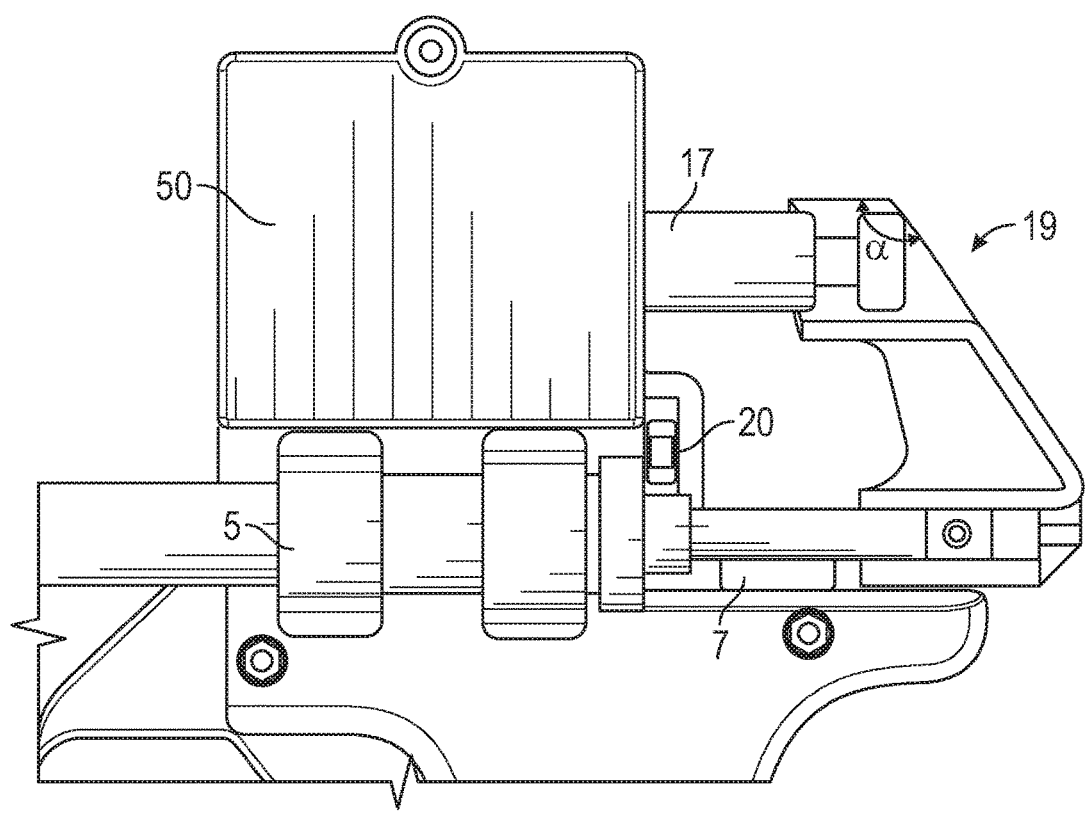
FIG. 2B shows an enlarged view of a portion of the device (1), with emphasis on the piston pusher (19), the air cylinder (50), the air cylinder rod (17) and the rail or piston pusher guiding means (7)

That said, the choice to position the pneumatic cylinder above the injectors caused significant engineering challenges. Applicants' initial efforts to actuate the injectors from above led to unacceptable motion and friction. Faced with this new and unexpected problem, Applicants developed the guiding means (7), made of a particular material, which minimizes the friction between it and the piston pusher (19), and contributes to smooth, lateral movement of the pistons (40). In an embodiment, the guiding means (7) and the piston pusher (19), particularly where it physically contacts the guiding means (7), are made of compatible polymeric materials, to provide for smooth, low-friction, slidable engagement between the components. Moreover, Applicants have surprisingly found that the geometry of the push component (19) is particularly important to managing the forces resulting from a top-mounted pneumatic actuator. Energetically favorable angles "α" are from about 110° to about 140°, from about 115° to about 135°; from about 120° to about 130°; or about 135° (see FIGS. 2A & 2B).

Accordingly, the push of the injectors (30) is accomplished by the actuation of the pneumatic cylinder (50), which laterally moves the pneumatic cylinder rod (17), in a direction parallel to the configuration of the injectors (30), such that actuation of pneumatic cylinder moves the injectors laterally, within a stroke distance equal to the stroke distance traveled by the pneumatic cylinder rod (17).

When the powered injector device (1) is in a standby position, the pneumatic cylinder rod (17) is extended to a maximum position, toward the rear of the device (1). When the device (1) is activated, by a user pulling the trigger (10), the cylinder rod (17) moves in toward the pneumatic cylinder (50) to which it is operably connected. Since the rod (17) is operably connected to the piston pusher (19), the motion of the rod (17) thereby drives the piston pusher (19) to slide on its guiding means (7), and push the pistons (40) of the injectors (30). The fluid substances contained in the injectors (30) is thereby dispensed/injected.

As indicated, the piston pusher (19) slides on a piston pusher guiding means (7). The guiding means may be, for example, in the form of a track, guide or rail. The guiding action provided by the guiding means (7) allows the piston pusher (19) to extend (away from the pneumatic cylinder and toward the user) and retract (toward the pneumatic cylinder), remaining perfectly straight and parallel with respect to the front-back axis of the device (1). This guided motion provides precise control of the injectors (30), including the pistons (40) integrated therein, to ensure delivery of consistent doses during each injection cycle.

Figure 9A:
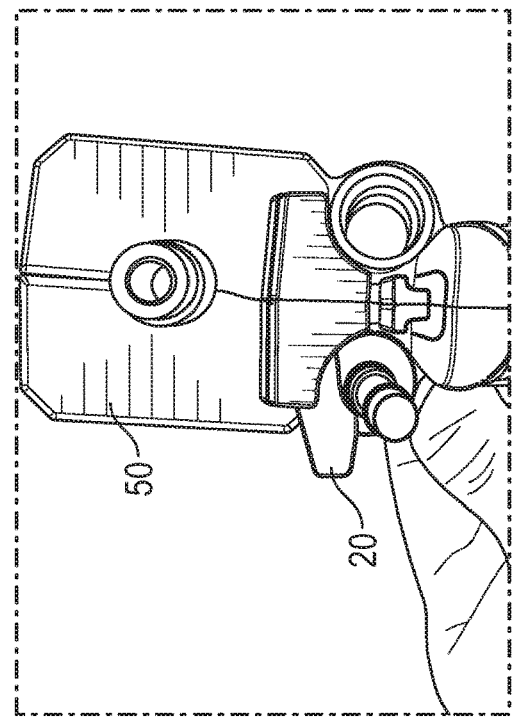
FIG. 9A is a rear view of the injection device (1) after one of the injectors (40) has been reattached (left). The locking key (20) may now be slidably moved to allow reattachment of the second injector (30) (right)
Figure 9A:
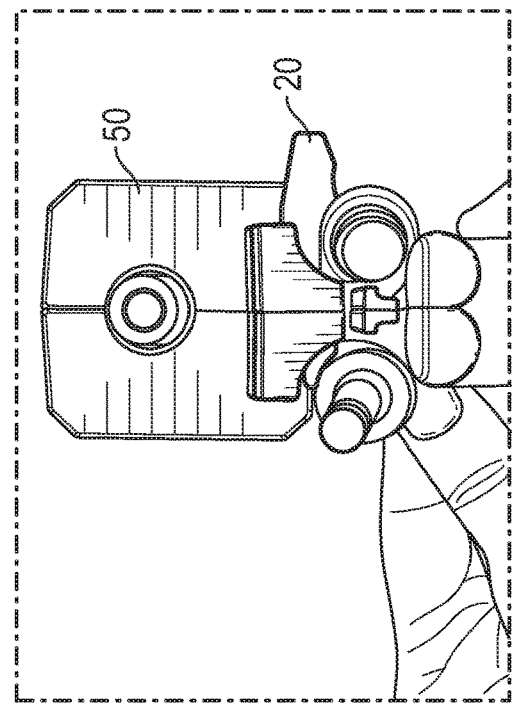
Figure 9B:
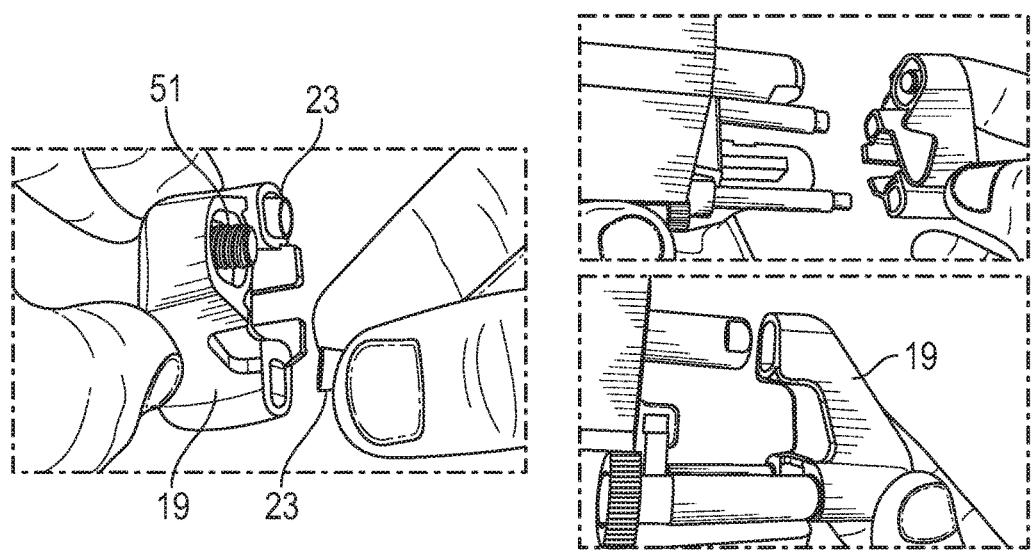
FIG. 9B shows the application (left) of shock absorbers (23) to the piston pusher (19) prior to its reattachment (right) to the air cylinder rod (17) and injectors (30). As indicated, the air cylinder rod (17) may be notched such that when connected to the pusher (19), the rod (17) is restricted from freely rotating.
Figure 9C:
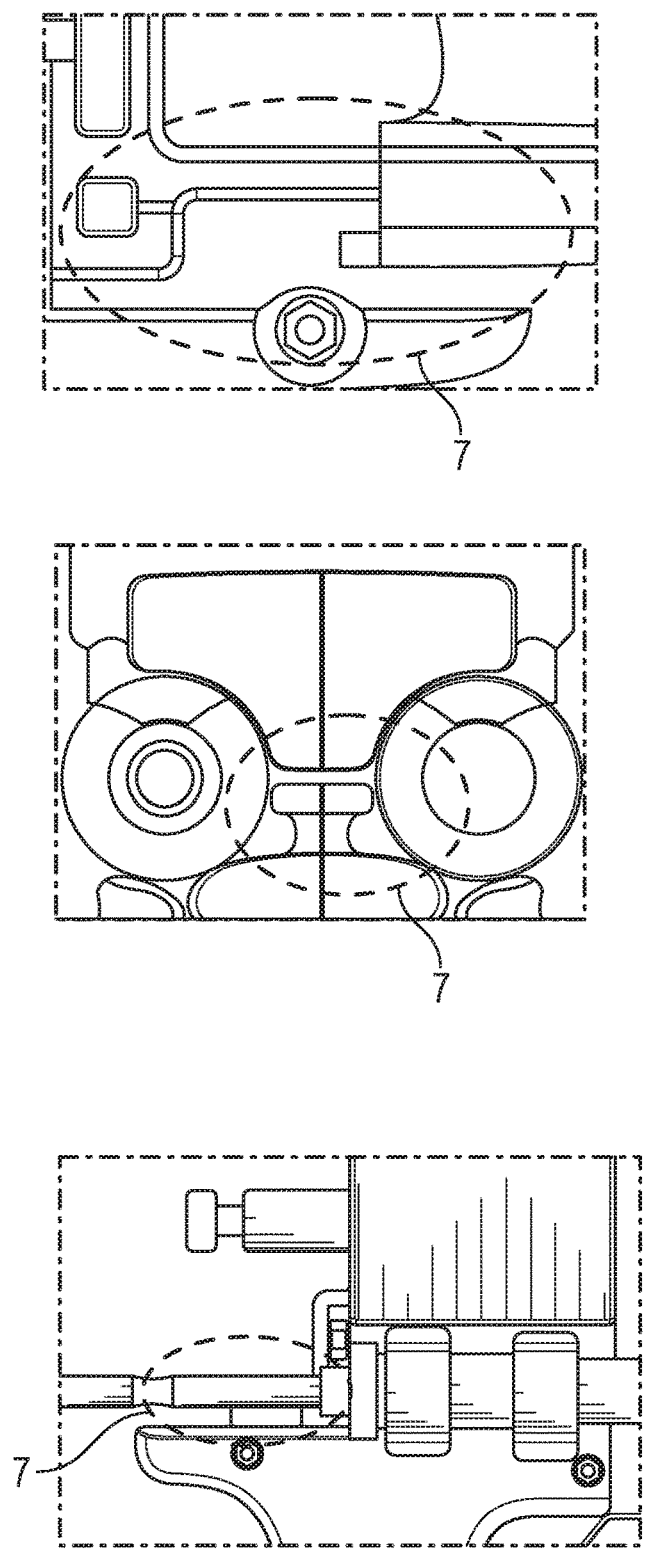
FIG. 9C shows several views highlighting the piston pusher guiding means (7)
Figure 10:
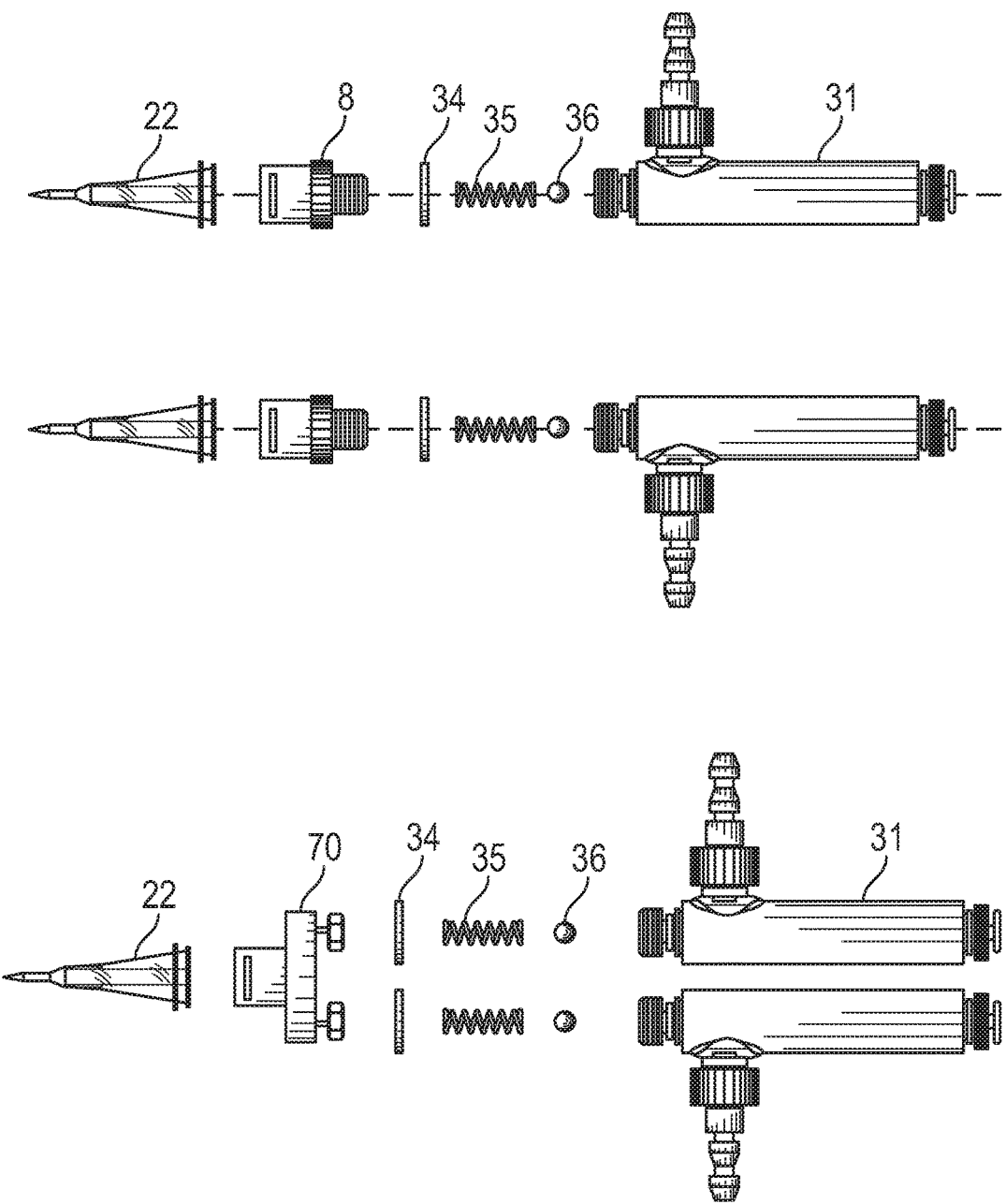
FIG. 10 shows how the device may be configured for use with two terminal needles (22) (top) or a single terminal needle (22) (bottom). In the single needle embodiment, adaptor (70) is in fluid communication with both injectors (30) such that when the two separate fluids/vaccines are pushed from the piston cylinder (31), they are combined in (70) and delivered/administered/injected as a single formulation at the needle (22).

In some embodiments, the powered injection device comprises a compensation system, which accommodates variations among the lengths of the various pistons (40), to improve the uniformity of dose/injection volume. For example, in cases where the piston (40) in the left injector (30) is 0.1 mm shorter than the piston (40) in the right injector (30), the presence of the shock absorbers (23) compensates for the minor difference. As shown in FIG. 9B, shock absorbers (23) may be placed in the bottom of the housing of the piston pusher (19), such that the shock absorbers are configured to be in physical contact with the piston pusher (19) and the piston rod (48). As such, the shock absorbers (23) reduce the shock between the piston pusher (19) and the piston rods (48) when the pistons reach the end position. Shock absorbers may be made of any suitable material known to skilled persons, including rubber, polymeric materials or even metallic material, as in metallic springs.

To obtain an optimum sliding of the piston pusher (19) on the guiding means (7), and to reduce component wear due to friction, the various pieces may be composed of different materials (i.e. the pusher and the guiding means are ideally not made of the same material). In some embodiments, the pusher (19) may be composed of an "oily" material and its corresponding guiding means (7) may be a rail composed of a hard material. Taking this approach, Applicants have provided pusher (19) and guiding means (7) combination that is essentially "self-lubricating." The skilled person can select many other "self-lubricating" combinations, now that this disclosure has been made.

In some embodiments, the disclosure provides a powered injection device, which may be powered, for example, by an air supply and a pneumatic cylinder, an hydraulic cylinder or electricity. Applicants envision that any suitable present or future means of supplying mechanical energy may be used in the practice of the invention, now that this disclosure has been made.

In some embodiments, the power device may comprise one or more injectors, each injector comprising an injector cylinder, a piston securing cylinder and a piston. The injector cylinder and piston securing cylinder may be in the form of a single component, or separate components. The device also comprises a source or means for providing mechanical energy, said mechanical energy providing means situated above the injector(s), for moving the pistons laterally inside the injector(s).

In some embodiments, the device further comprises a piston pusher, which operably connects the mechanical energy providing means to the piston(s). The device may also comprise a pusher guide means, for maintaining the pusher in a parallel orientation, with respect to the injector (s), while the piston is being moved by the action of the energy providing means.

In some embodiments, the device comprises and is powered by a pneumatic cylinder, situated above the injector(s), wherein when a pressurized air supply is connected to the device, the pneumatic cylinder extends a cylinder rod, which moves the pusher, which moves the piston(s) to a resting position.

In some embodiments, the device may comprise a trigger, a button, or other activating means, which is operably connected to the pneumatic cylinder, wherein when the trigger is pressed, the cylinder retracts the cylinder rod, moving the piston(s) from the resting position to an injection position.

In some embodiments, the device comprises two injectors, each comprising a needle connecting means, an injector cylinder, a piston securing cylinder and a piston; wherein, when the trigger, button or other activating means is actuated, each piston sealably slides into its corresponding injector cylinder, pushing fluid from the injector cylinder out through the needle connecting means. When a fluid supply is connected to the device, and when the pressurized air supply is connected to the device, and when the pistons are moved to their resting positions, fluid may be drawn through a fluid inlet into the injector cylinders. In addition, when the trigger, or button or other activating means is actuated, the pistons move from their resting positions to their injection positions, and a one-way valve prevents the fluid from being pushed by the pistons from the injector cylinder back through the fluid inlet. Conversely, when the trigger, button or other activating means is released, the pistons move from their injection positions to their resting positions, and a one-way valve prevents the fluid from being pulled by the pistons from the needle connecting means back into the injector cylinder.

In some embodiments, when the pistons retract toward the back of the device, the fluid flows into injector cylinder through the fluid inlet.

In still other embodiments, the device has a minimum operating pressure of about 4 bars.

In another aspect, the disclosure provides a method of injecting an animal with a fluid comprising the step of injecting the animal with the device of any one of the proceeding claims. The animal may be an avian animal, including a day-old chick.

In an embodiment of the method, the fluid may be an immunological composition.

In some embodiments, the composition is a vaccine, meaning that it elicits in an animal a protective immune response against subsequent challenge or exposure to the virulent form of the agent or pathogen against which the vaccine has been designed to protect.

In some embodiment, two vaccines are delivered to the animal with each injection. In some embodiments, the two vaccines are injected into the animal using two terminal needles, one needle for each vaccine. In other embodiments, the two vaccines are combined in an adaptor, such that the injection is accomplished using only a single terminal needle.

In some embodiments, at least one of the vaccines comprises more than one valency.

In other embodiments, each vaccine contains only a single valency.

In some embodiments, the vaccine protects an avian against one or more of the following avian diseases or infections: Newcastle disease, infectious bronchitis, infectious bursal disease, herpesvirus, egg-drop syndrome or avian influenza.

The invention is further illustrated by the following non-limiting examples.

Examples

Detailed Description of the Primary Embodiment

Figure 3A:
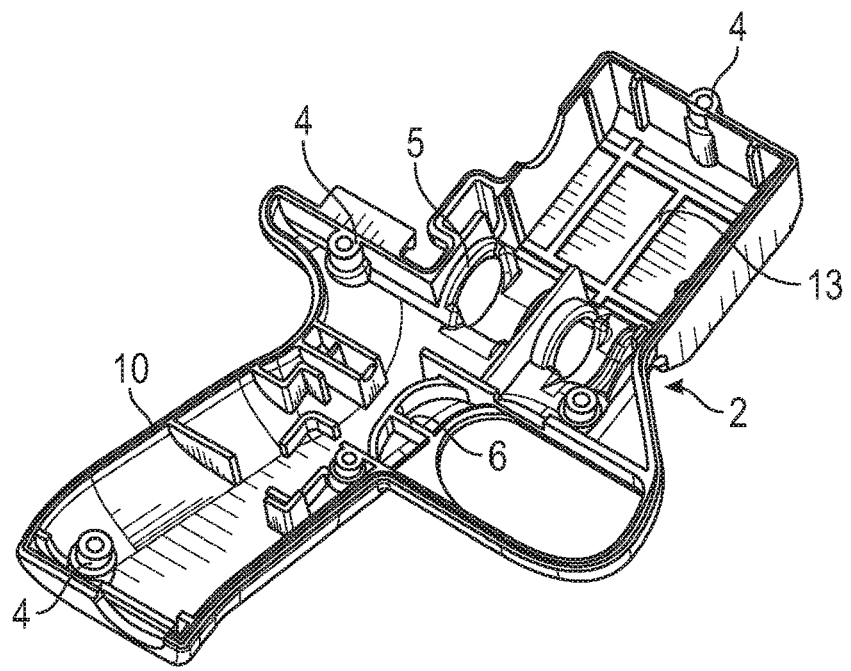
FIG. 3A shows a left portion (2) of the device housing.
Figure 3B:
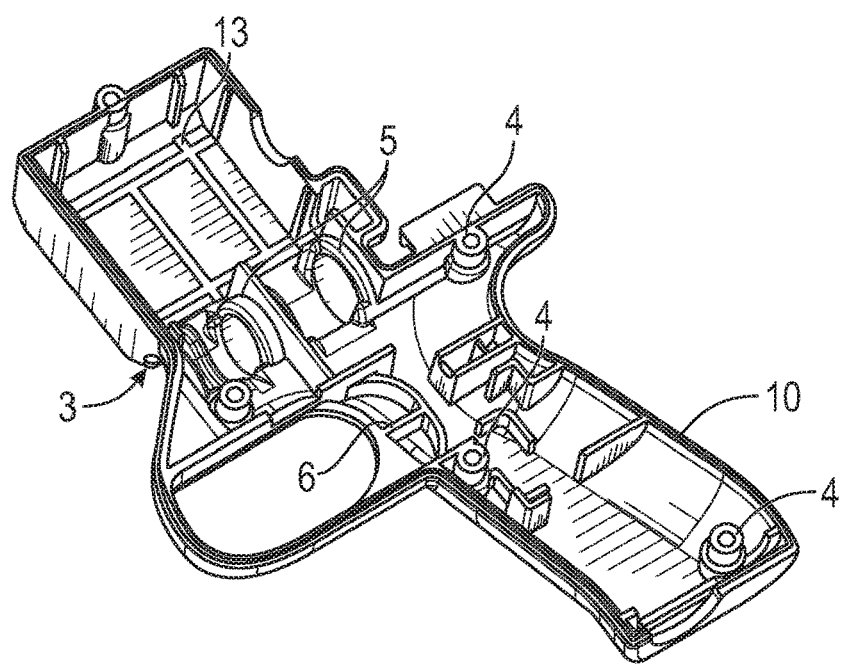
FIG. 3B shows a right portion (3) of the device housing.
Figure 5A:
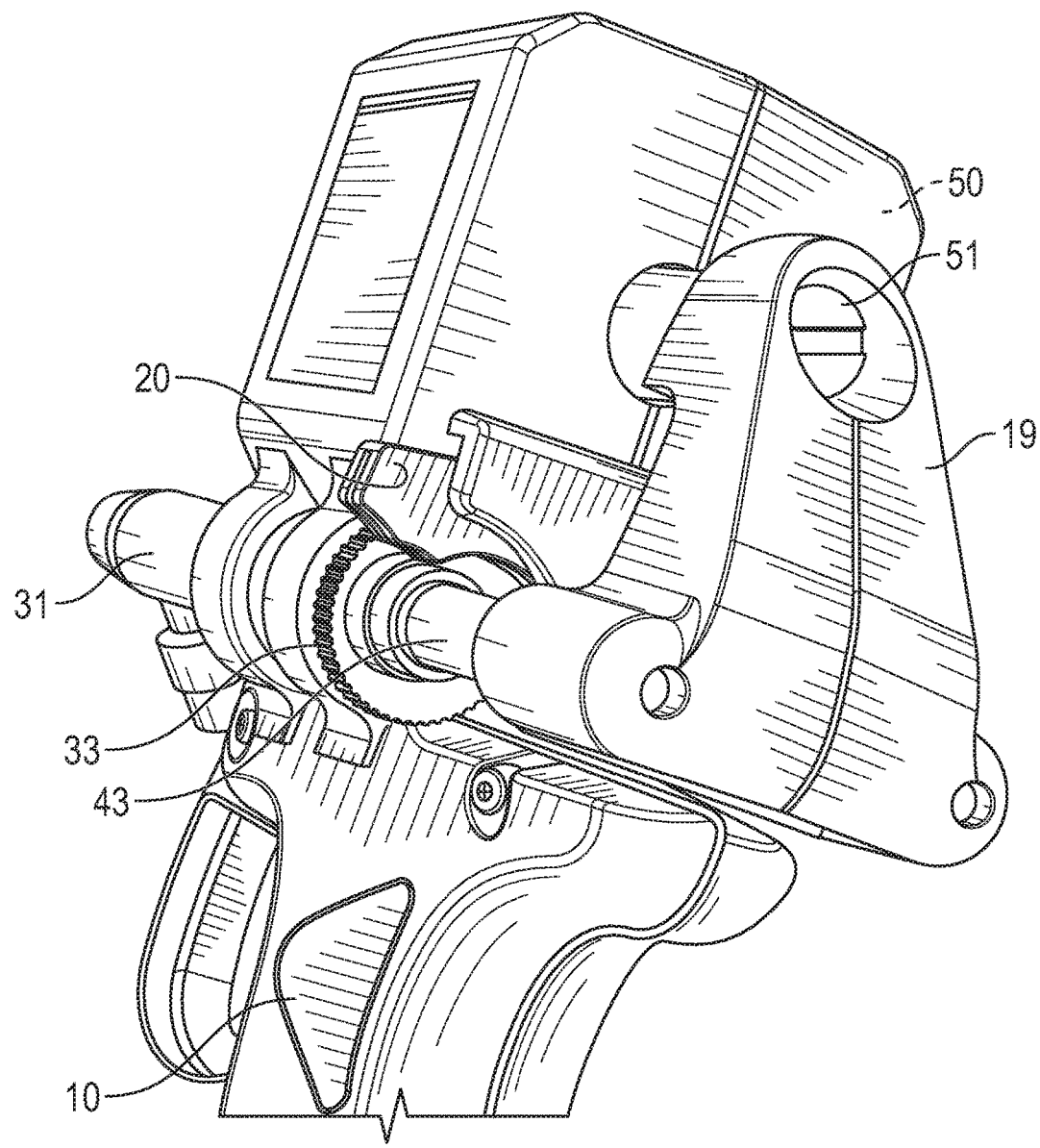
FIG. 5A is the first in a series of drawings depicting how a user may prepare the powered injection device (1) for use. To remove the piston pusher (19), the user begins by unscrewing holding screw (51). Next, the user presses one side of the locking key (20) to free the injector (30) for subsequent removal.
Figure 5C:
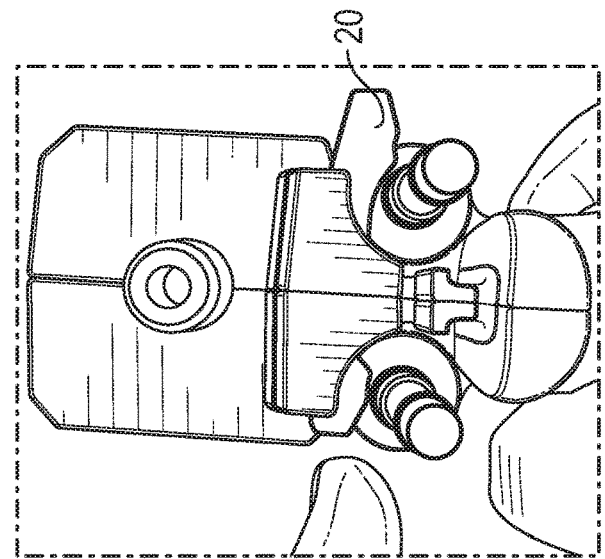
FIG. 5C shows the device with its locking key (20) in the unlocked position, allowing removal/replacement of the left injector (30)
Figure 5B:
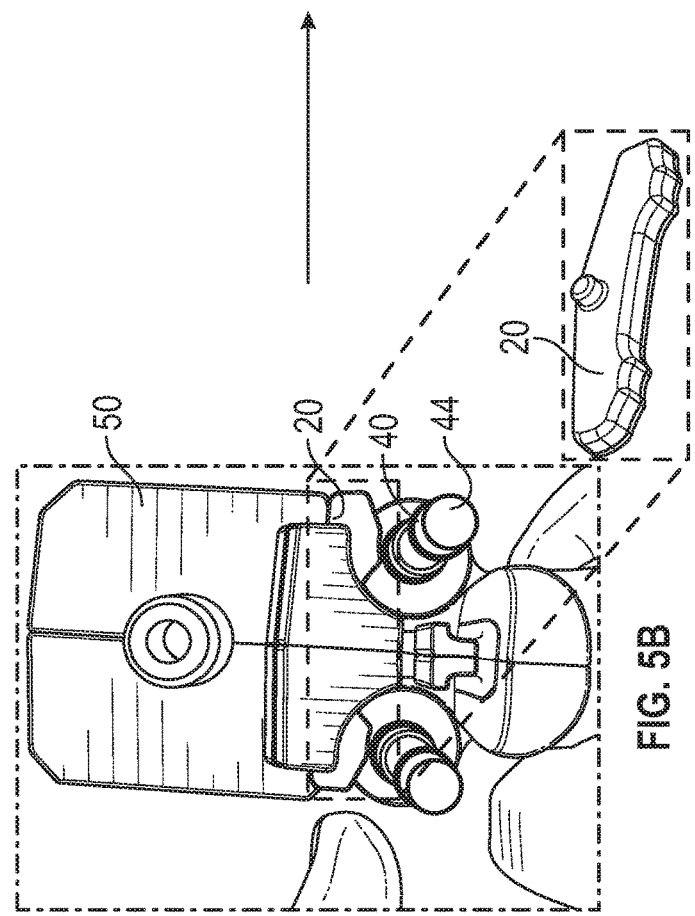
FIG. 5B shows the device (1) with its locking key (20) in the locked position. Disassembly may be accomplished beginning with either injector (30) first (i.e. a user may push to the right to release the left injector or push to the left to release the right injector first)
Figure 6A:
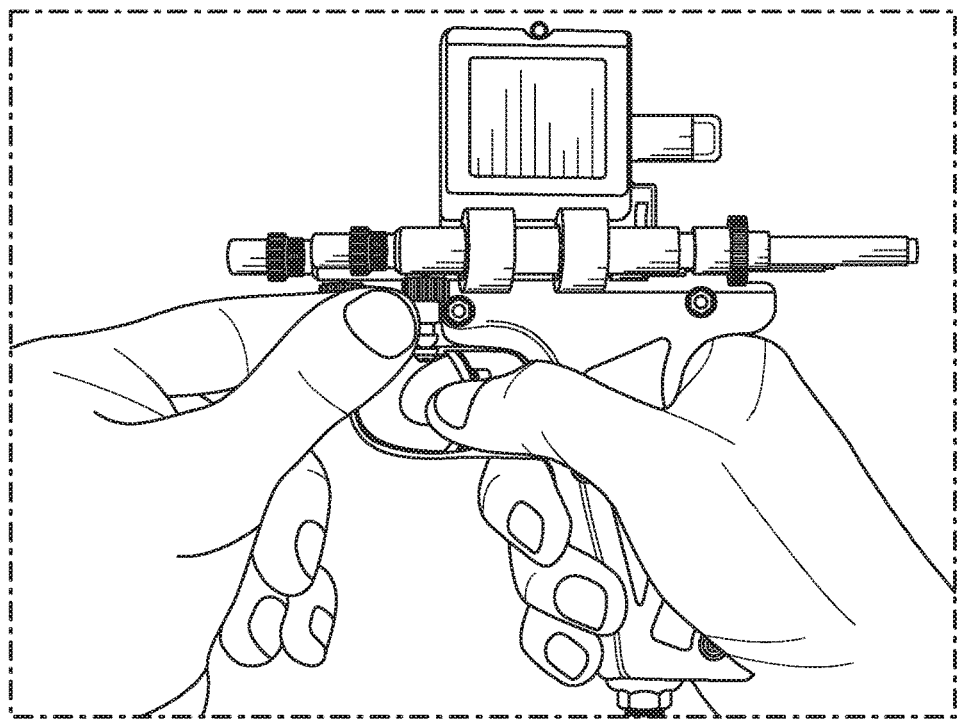
FIG. 6A is the first in a series of drawings showing how to remove an injector (30) once the pusher (19) has been removed. To remove the injector (30), the user first grasps the injector gripping means (33), and pulls the injector (30) toward the back of the device (1)
Figure 6B:
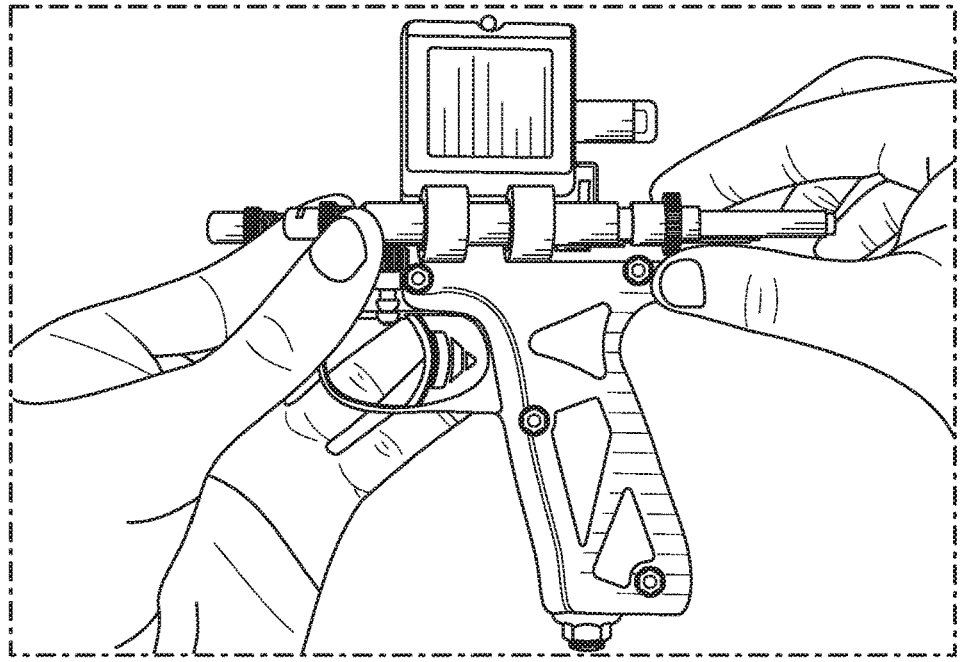
FIG. 6B shows a user's right hand grasping the injector gripping means (33), while holding the injector cylinder (31), to unscrew the piston securing cylinder (32), which circumscribes and contains the piston (40)
Figure 6C:
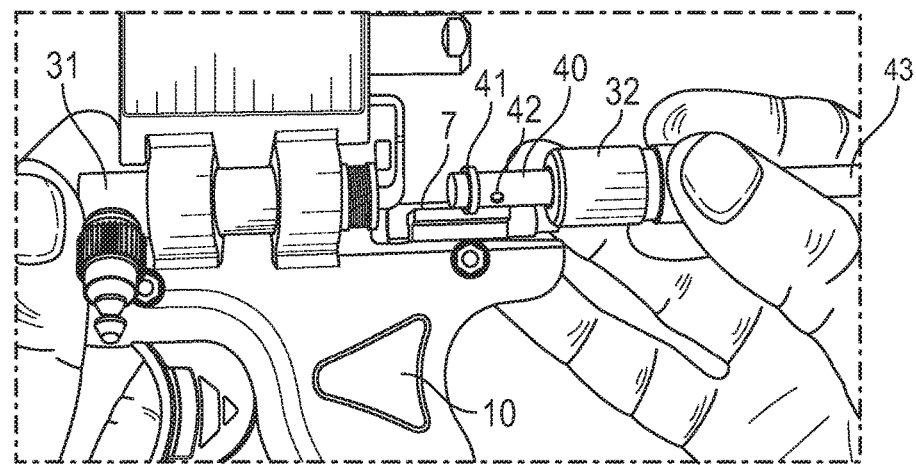
FIG. 6C shows the piston (40) (still attached to the rear portion of the injector) released from the front portion of the injector (31)

In an embodiment, the apparatus comprises a powered injection device, which resembles a gun (FIG. 1). In one embodiment, the powered injection device (1) comprises a housing consisting of a left (2) and right half (3), as depicted in FIGS. 3A and 3B. The housing halves (2, 3) are reversibly attachable to one another, and are configured to receive and contain the components of the powered injection device (1). The housing comprises a handle (10), orifices (4) through which assembly/disassembly screws (14) may be affixed, to secure the two housing halves. The housing further comprises a trigger receiving portion (6), an injector receiving means (5), to receive and hold one or more injectors (30), and a pneumatic cylinder housing portion (13), to receive and hold a pneumatic cylinder (30). The pneumatic cylinder holder (13) comprises an orifice (15), through which the pneumatic cylinder rod (17) may pass, as shown for example in FIGS. 1 and 5A. The housing also comprises an orifice (16), which is configured to receive an air supply, which powers the pneumatic cylinder (50). Conduits to communicate pneumatic energy may be arranged in any suitable manner, for example, that depicted in FIG. 2A. There, conduit (9) is configured to supply pneumatic pressure to pneumatic cylinder (50), such that when the trigger (12) is pulled by a user, the cylinder (50) moves the pusher (19), which moves the piston (40) rod, which causes fluid to be dispensed through needle connecting means (38). The trigger (12) is thus operably connected to the pneumatic cylinder (50).

Figure 4:
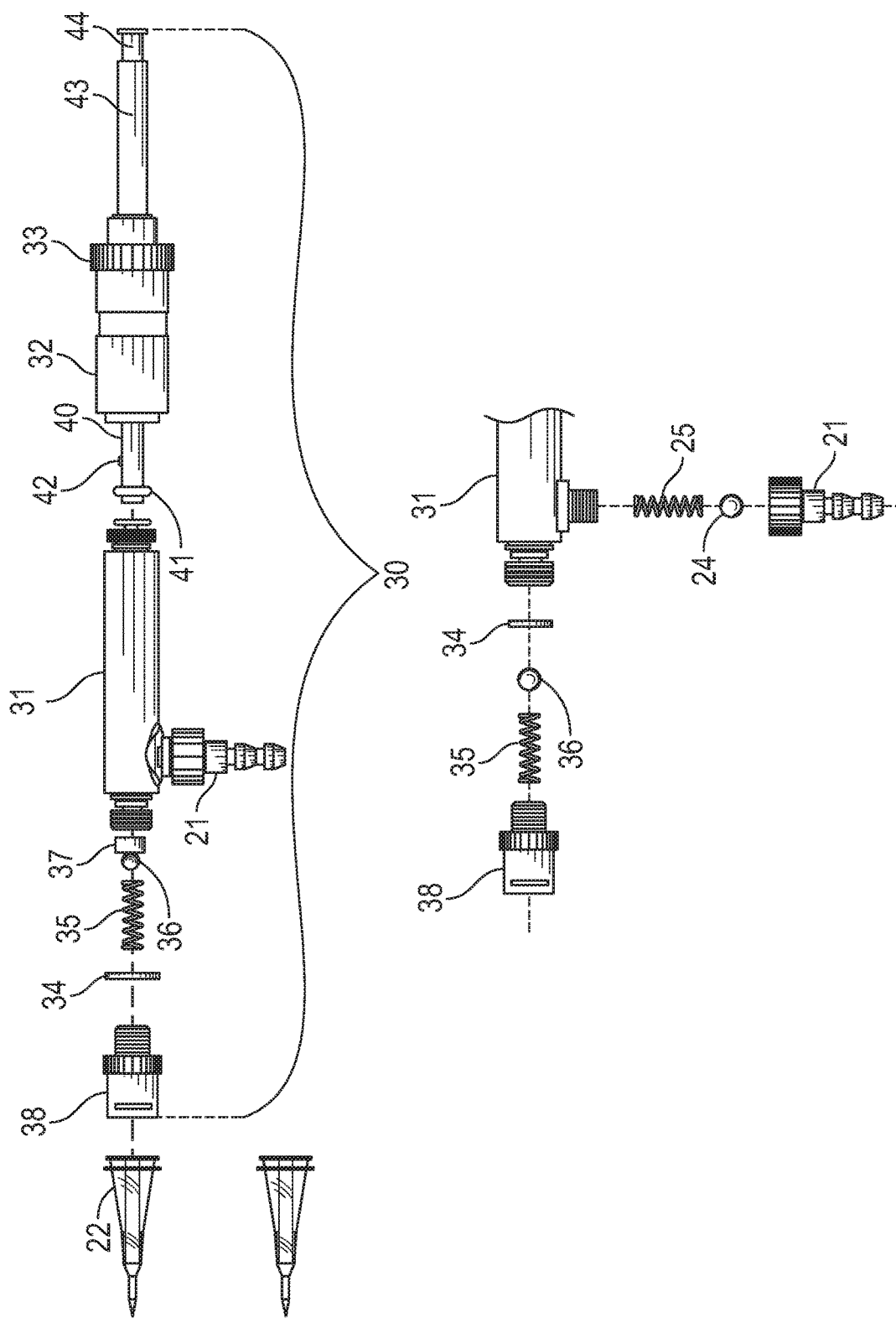
FIG. 4 shows an injector assembly (30)

In this embodiment, the powered injection device (1) is thus a pneumatically actuatable injector, having the ability to contain and direct the action of two injectors (30). Each injector (30) generally comprises a needle connecting means (38), an injector cylinder (31), a piston securing cylinder (33) and a piston. The needle connecting means (38) may be sealably connected to the injector cylinder (31) via a one-way valve means. As shown in FIG. 4, the one-way valve means may comprise a gasket (34), a spring (35), a ball barring (36) and a second gasket (37). Other routine one-way valve configurations are envisioned, including a polymeric umbrella-type valve. The injector cylinder (31) is also connectable to a fluid/vaccine supply line connector (21), which contains a similar one-way valve configuration. As shown in FIG. 4, connector (21) is sealably connected to injector cylinder (31) via a ball baring (24) and a spring (25). Thusly configured, fluid/vaccine may enter the injector cylinder (31) via the connector (21) when the pressure is greater at (21) than it is inside cylinder (31). Conversely, fluid moves from cylinder (31) when the pressure is greater inside the cylinder (31) than it is inside needle connecting means (38).

Figure 7A:
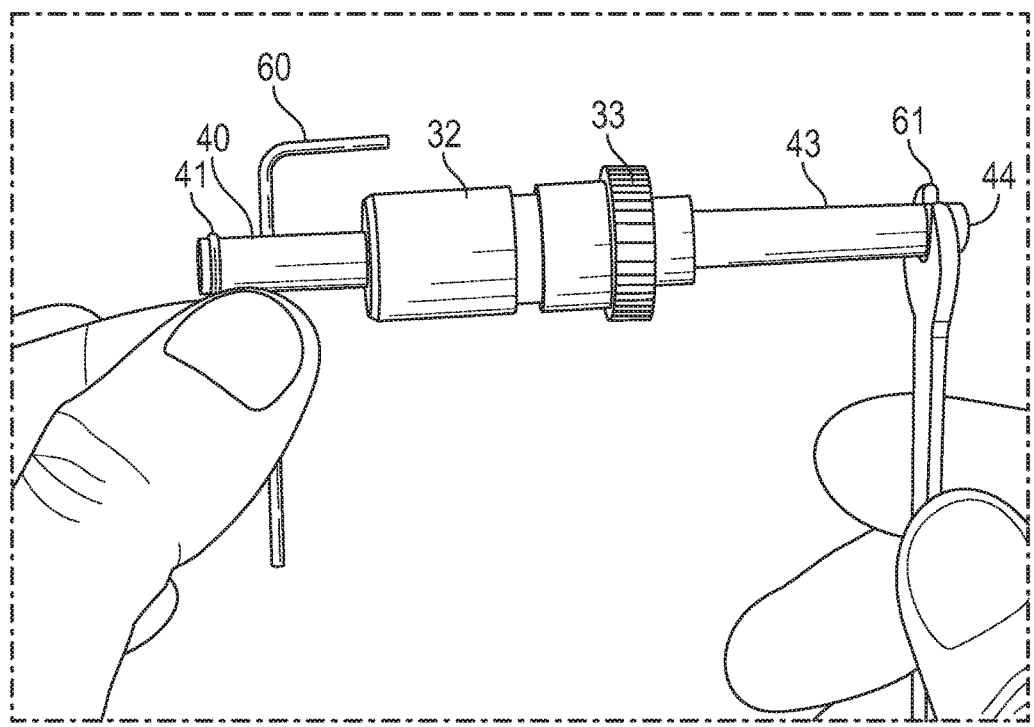
FIG. 7A shows how to remove a piston from the piston securing cylinder (32). An Allen wrench (60) and conventional wrench (61) may be used in combination to unscrew the piston (40) from the piston nut (44)
Figure 7B:
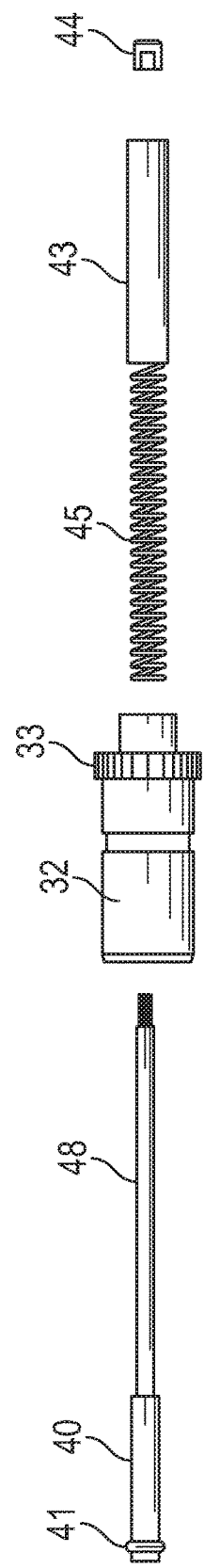
FIG. 7B shows the piston (40) completely removed from the piston securing cylinder (32)
Figure 8A:
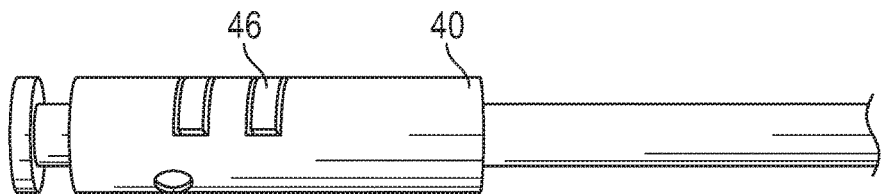
FIG. 8A is the first in a series of drawings showing how a user may reassemble the piston (40) back into the injector (30). This view shows an engraved marking (46), which indicates the volume injected by this particular piston (40)
Figure 8B:
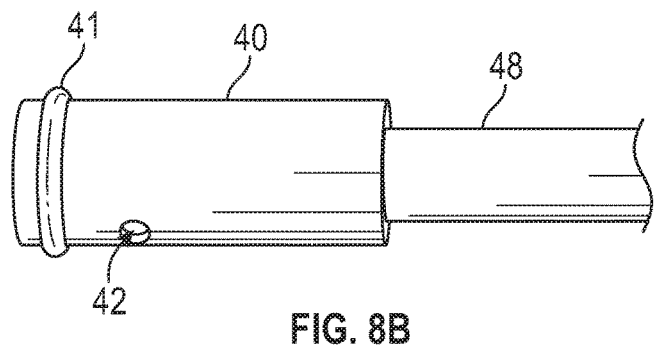
FIG. 8B shows the piston with the piston gasket (41) attached.
Figure 8C:
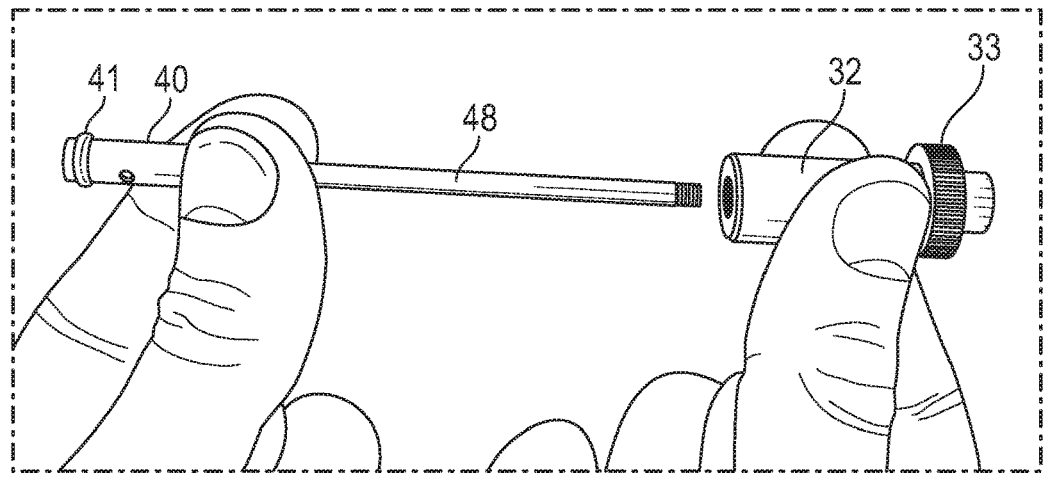
FIG. 8C shows a user's hands preparing to insert the piston (40) into the piston securing cylinder (32)
Figure 8D:
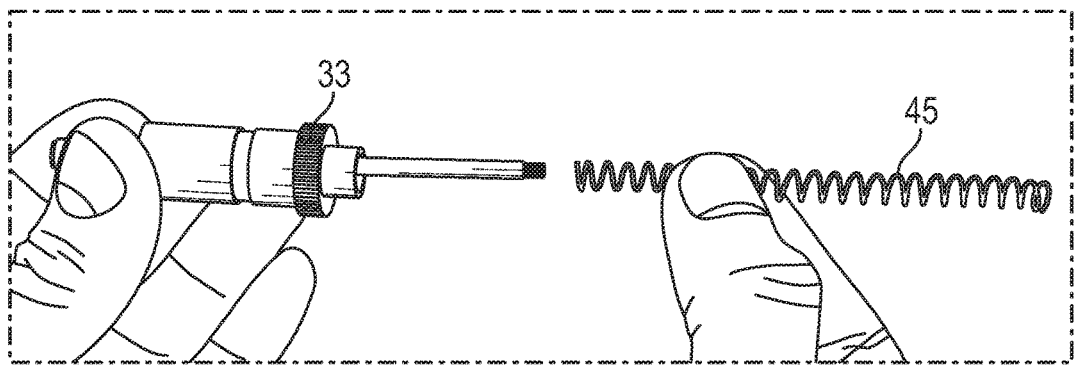
FIG. 8D shows a user's hands preparing to insert the piston (40) into the piston spring (45), after having inserted the piston through the piston securing cylinder (32)
Figure 8E:
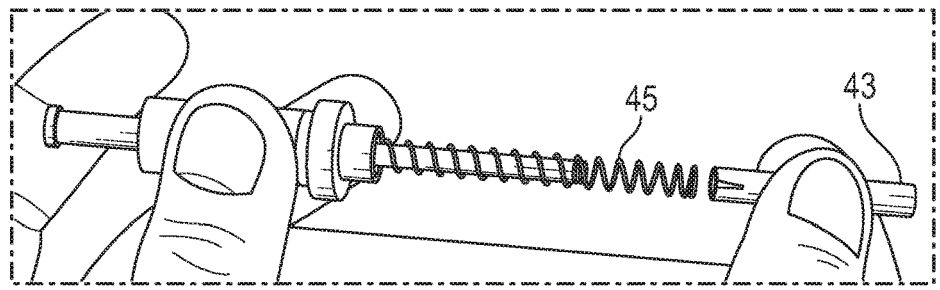
FIG. 8E shows a user's hands preparing to enclose the piston (40) with the piston sleeve (43), and compress the piston spring (45) within the sleeve (43)
Figure 8F:
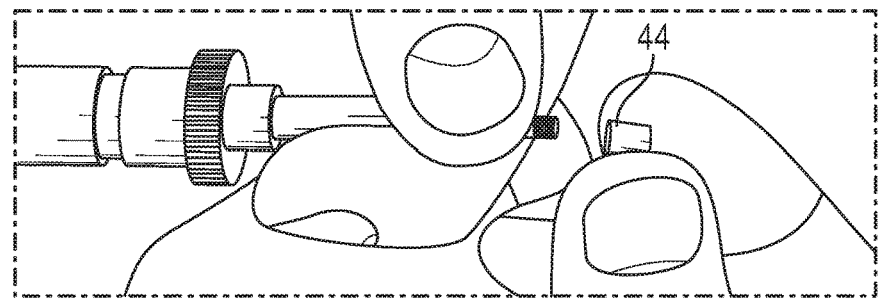
FIG. 8F shows a user's hands preparing to attach the piston nut (44) to the piston sleeve (43)
Figure 8G:
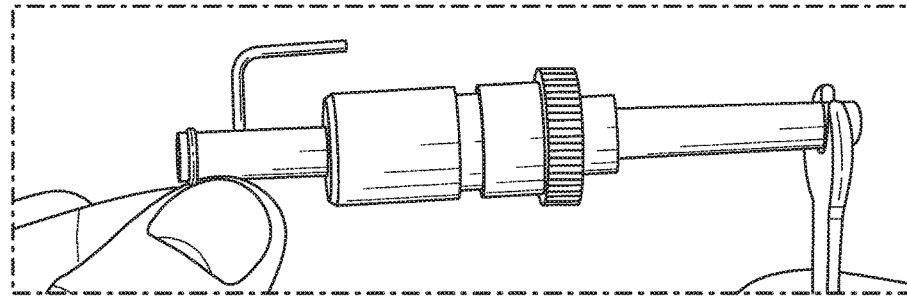
FIG. 8G shows the reassembled injector (30)
Figure 8H:
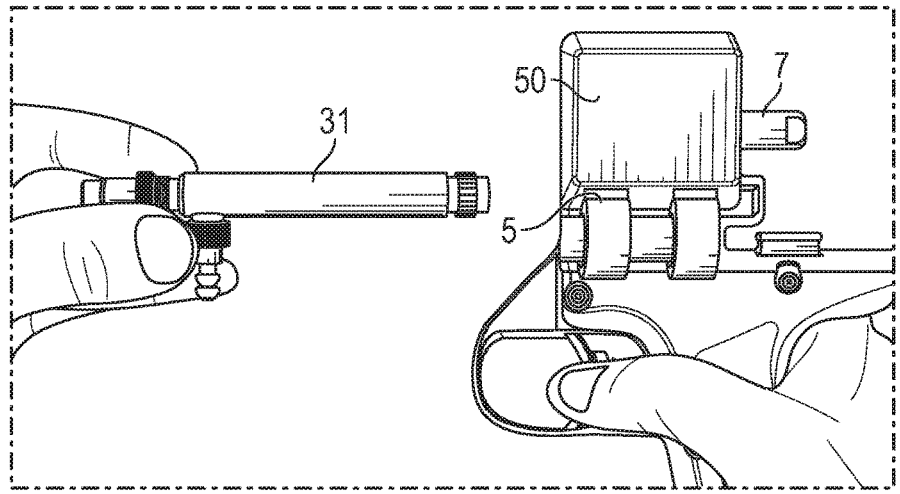
FIG. 8H shows a user's hands preparing to insert the injector cylinder (31) into the injector retaining means (5)
Figure 8I:
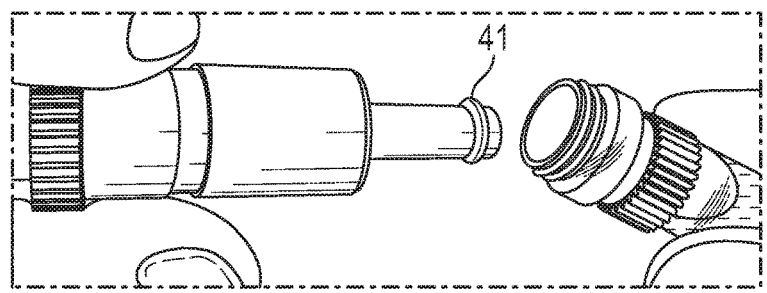
FIG. 8I shows how oil may be applied to the piston gasket (41)
Figure 8J:
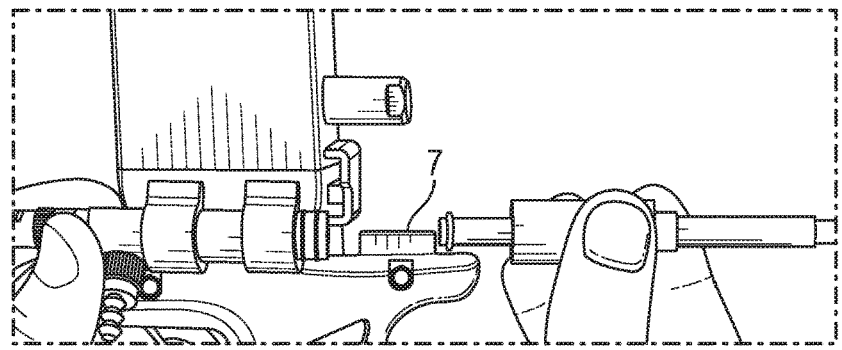
FIG. 8J shows a user's hands preparing to connect the piston (40), which is attached to the piston securing cylinder (32) to the injector cylinder (31). The piston securing cylinder (32) connects to the injector cylinder (31) near the injector retaining means (5)
Figure 8K:
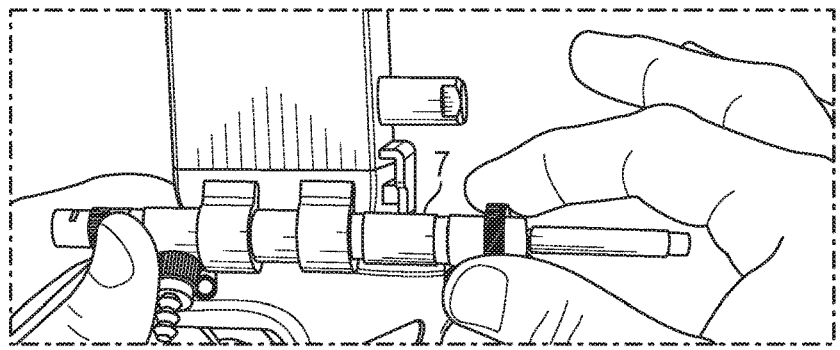
FIG. 8K shows the injector (30) reassembled onto the device (1)
Figure 8L:
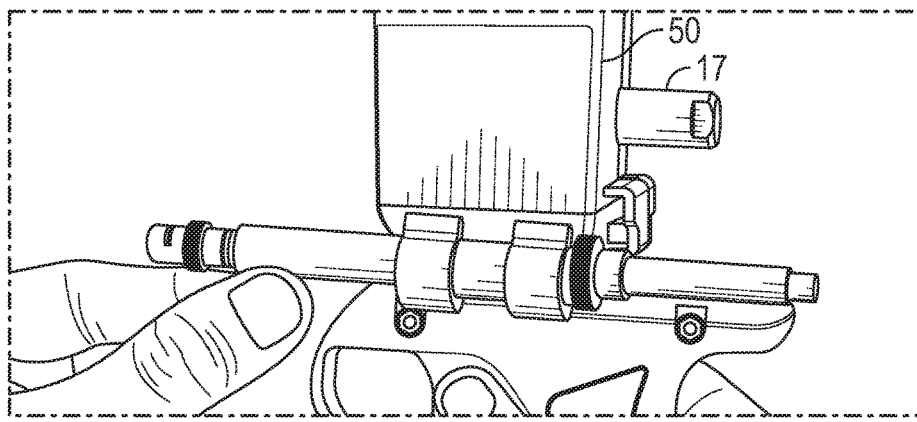
FIG. 8L shows the injector (30) pulled forward, in a "ready-to-inject position"

Further, as shown in FIGS. 7A to 7B, and in FIGS. 8A to 8L, the injector cylinder (31) is configured to connect via threading to a piston securing cylinder (32). The securing cylinder may comprise a gripping means (33) and a "tool hole" (42) to facilitate the exchange of one size/type piston (40) for another. The piston (40) attaches to the piston securing cylinder (32) via insertion into a piston sleeve (42) and attaching to the piston rod (48) of a piston nut (44). Now connected to the securing cylinder (32), as shown in FIG. 7A, the piston (40) is inserted into the injector cylinder (31), which has already been inserted into the device's injector receiving means (5) (FIGS. 8J to 8L). As shown in FIGS. 9A and 9B, once a first injector (30) is mounted into the device housing, the locking key (20) is moved to an unlocked position to allow the second injector (30) to be mounted. The locking key (20) is then moved into its locked position, and the device (1), equipped with both injectors (30), is now ready to be connected to a fluid/vaccine supply and begin injection cycles.

In another aspect, the disclosure provides methods of vaccinating animals, including injecting animals using the powered injection device of the present disclosure.

The invention will now be described by the following set of non-limiting claims.

What is claimed:

1. A powered injection device comprising:
   a body,
   an injector which comprises an injector cylinder mounted to the body, a piston securing cylinder mounted to the body and a piston in coaxial alignment with the injector cylinder and the piston securing cylinder, the piston configured to be slidable inside the injector cylinder;
   a piston pusher in operable communication with the piston; and
   a guide means configured to maintain coaxial alignment of the piston, piston securing cylinder and the injector cylinder as the piston slides inside the piston securing cylinder and injector cylinder; and wherein the device is powered by a pneumatic cylinder and rod coupled to the piston pusher, wherein the rod is substantially parallel to the axis of the coaxially aligned piston, piston securing cylinder and injector cylinder; and wherein the injector cylinder comprises a fluid inlet in fluid communication with a fluid supply, wherein the fluid inlet is in fluid communication with a first one-way valve configured to prevent fluid backflow toward the fluid supply.

2. The device of claim 1, further comprising a trigger mounted on the body, operably connected to the pneumatic cylinder and configured to actuate the pneumatic cylinder and rod.

3. The device of claim 1 wherein a seal is positioned between the piston and injector cylinder.

4. The device of claim 1, comprising a second one-way valve configured to prevent fluid backflow toward the injector cylinder from a needle connecting means in fluid communication with the injector cylinder.

5. A method of injecting an animal with a fluid comprising the step of injecting the animal with the device of claim 1.

6. The method of claim 5, wherein the animal is an avian animal.

7. The method of claim 6, wherein the avian is a day-old chick.

8. The method of claim 7, wherein the fluid is an immunological composition.

9. The method of claim 8, wherein the fluid is a composition is a vaccine.

10. The method of claim 9, wherein two vaccines are delivered to the animal with each injection.

11. The method of claim 10, wherein the two vaccines are injected into the animal using two terminal needles, one needle for each vaccine.

12. The method of claim 11, wherein the two vaccines are combined in an adaptor, such that the injection is accomplished using only a single terminal needle.

13. The method of claim 10, wherein at least one of the vaccines comprises more than one valency; or, wherein each vaccine contains only a single valency.

14. The method of claim 9, wherein the vaccine protects an avian against one or more of the following avian diseases or infections: Newcastle disease, infectious bronchitis, infectious bursal disease, herpesvirus, egg-drop syndrome or avian influenza.

15. The device of claim 1 comprising two parallel injectors mounted on the body and in mechanical communication with the piston pusher.

16. The device of claim 1 wherein the body is shaped as a pistol and pistol grip.

* * * * *